United States Patent [19]

Ferguson et al.

[11] Patent Number: 4,553,967
[45] Date of Patent: Nov. 19, 1985

[54] WOUND CARE AND DRAINAGE SYSTEM HAVING HAND ACCESS PORT

[75] Inventors: Keith Ferguson, Scotch Plains, N.J.; Nancy McClees, Worthington, Ohio

[73] Assignee: E. R. Squibb & Sons, Inc., Princeton, N.J.

[21] Appl. No.: 541,823

[22] Filed: Oct. 14, 1983

[51] Int. Cl.[4] .............................................. A61M 1/00
[52] U.S. Cl. ................................... 604/317; 128/767; 604/334; 604/344
[58] Field of Search ............... 604/317, 319, 327, 332, 604/334, 336, 337, 338, 339, 341, 343, 344; 128/760, 767, DIG. 24; 383/41, 42, 66

[56] References Cited

U.S. PATENT DOCUMENTS

| Re. 29,319 | 7/1977 | Nordby et al. ..................... 128/275 |
| 3,568,675 | 11/1971 | Harvey ................................. 128/275 |
| 3,874,387 | 4/1975 | Barbierri .............................. 128/325 |
| 4,023,569 | 5/1977 | Warnecke et al. ................... 128/154 |
| 4,095,589 | 6/1978 | Manschot et al. ................... 128/767 |
| 4,224,941 | 9/1980 | Stivala ............................. 128/207.26 |
| 4,250,882 | 2/1981 | Adair .................................. 128/275 |
| 4,421,509 | 12/1983 | Schneider et al. .................. 604/327 |
| 4,460,363 | 7/1984 | Steer et al. .......................... 604/336 |
| 4,468,227 | 8/1984 | Jensen ................................. 604/327 |

FOREIGN PATENT DOCUMENTS

| 1549756 | 8/1979 | United Kingdom . |
| 1571657 | 7/1980 | United Kingdom . |
| 2099308 | 12/1982 | United Kingdom . |

Primary Examiner—C. Fred Rosenbaum
Assistant Examiner—J. L. Kruter
Attorney, Agent, or Firm—Lawrence S. Levinson; Stephen B. Davis

[57] ABSTRACT

A pouch having a bottom wall secured to an adhesive layer that can be cut to fit around a wound or surgical opening, gusseted side walls, and a top wall provided with one or more access openings. An irrigation port and a catheter access port can be secured to these top wall openings. The bottom wall extends beyond the adhesive layer and is provided with a large exit port oriented so that gravity will drain wound exudate from the pouch. This exit port is also large enough to accommodate a hand to aid in locating the pouch on the body and permit access to the wound site without removing the pouch from the body.

18 Claims, 4 Drawing Figures

WOUND CARE AND DRAINAGE SYSTEM HAVING HAND ACCESS PORT

BACKGROUND OF THE INVENTION

Jensen in U.K. Patent Application No. 2,099,308 discloses a wound drainage device in the form of a flexible pouch having top and bottom walls and pleated side walls that allow the top wall to be lifted a limited distance without transmitting appreciable lifting forces to the bottom wall when the bottom wall is surgically apertured and secured about a wound site. The top wall includes an access opening having a flanged locking ring of flexible plastics extending thereabout. A removable closure cap is attached to the access opening, the cap having a flat rim of flexible plastics with circumferential locking ribs releasably and sealingly engaging a series of mating ribs provided by the flanged portion of the ring.

Nordby et al. in U.S. Pat. No. Re. 29,319 disclose a wound drainage system which includes a drainable pouch having an apertured wall provided with an annular adhesive patch for securing the pouch to a patient in an area surrounding the wound site. The opposite wall of the pouch is provided with an access opening, and a transparent cap is adhesively secured to the pouch about that opening. When access to the wound is required for surgical examination, drain adjustment, wound treatment, or any other reason, the pressure-sensitive adhesive seal between the cap and pouch is broken and the cap is temporarily removed.

Other wound drainage and treatment devices are disclosed by Westaby et al. in British Pat. No. 1,549,756, Harvey in U.S. Pat. No. 3,568,675, Barbieri in U.S. Pat. No. 874,387, Warnecke et al. in U.S. Pat. No. 4,023,569, Stivala in U.S. Pat. No. 4,224,941, and Adair in U.S. Pat. No. 4,250,882.

SUMMARY OF THE INVENTION

This invention is directed to a pouch type wound care and drainage system. The pouch includes a bottom wall secured to an adhesive layer which can be cut to fit around the wound or surgical opening, gusseted side walls, and a top wall provided with one or more access openings. Means are provided for securing an irrigation port and a catheter access port to these top wall openings. Also, the bottom wall extends beyond the adhesive layer and is provided with a large exit port oriented in such a manner that gravity will drain wound exudate from the pouch. This exit port is also large enough to accomodate the average size hand to aid in locating the pouch on the body and permit access to the wound site without removing the pouch from the body.

DETAILED DESCRIPTION OF THE INVENTION

Figure 1:
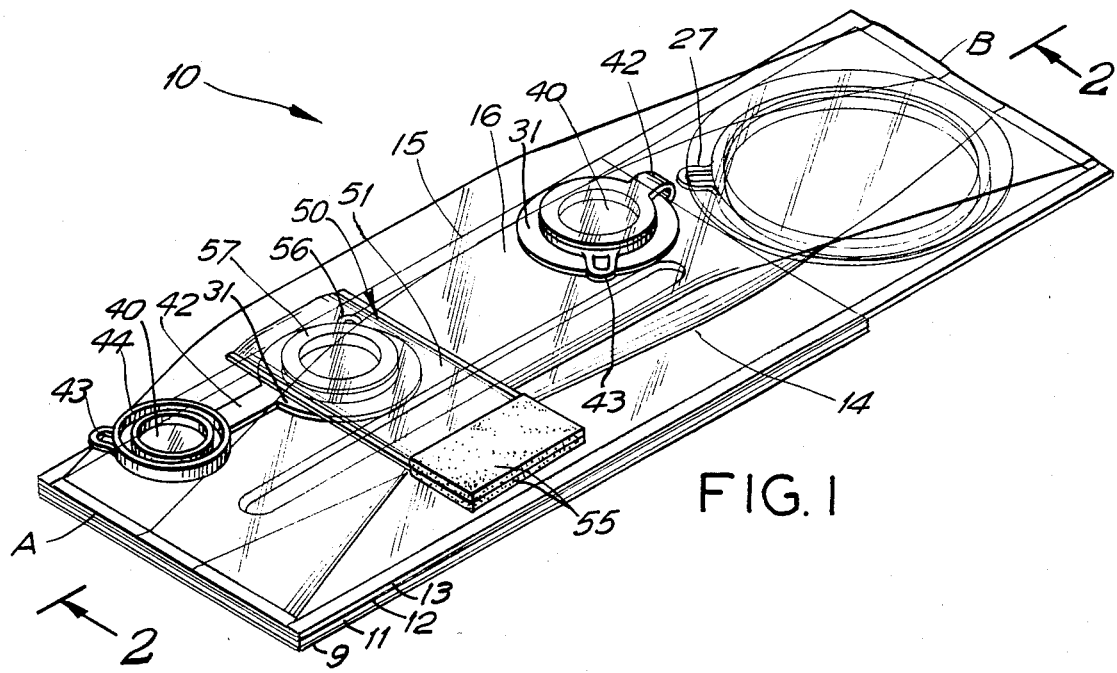
FIG. 1 is a perspective view of the wound care and drainage pouch of this invention.

This invention is directed to a pouch type wound care and drainage system. The pouch 10 includes a bottom wall 13, a top wall 16 and gusseted side walls 14 and 15. Top wall 16 is joined to bottom 13 along edges A and B by heat sealing or other means. Preferably, the pouch walls are formed from an odor proof, moisture proof, flexible, transparent, polymeric film material such as polyethylene.

Pouch 10 includes a layer of medical grade pressure sensitive adhesive 11 for attaching the device to the body of the patient. Adhesive layer 11 can be attached directly to bottom pouch wall 13. Preferably, adhesive layer 11 includes a thin film 12 of water insoluble polymeric material such as polyethylene and bottom pouch wall 13 is attached to film 12 by an aggressive adhesive. The exposed bottom surface of adhesive 11 is covered by silicone coated release paper 9 until the pouch is to be applied.

Adhesive layer 11 is preferably a homogeneous blend of one or more water soluble or swellable hydrocolloids such as gelatin, pectin, guar gum, sodium carboxymethylcellulose, etc. dispersed in a viscous elastomeric binder such as polyisobutylene as described by Chen in U.S. Pat. No. 3,339,546. Optionally, the adhesive layer can also include one or more cohesive strengthening agents as described by Chen et al. in U.S. Pat. No. 4,192,785.

Figure 2:
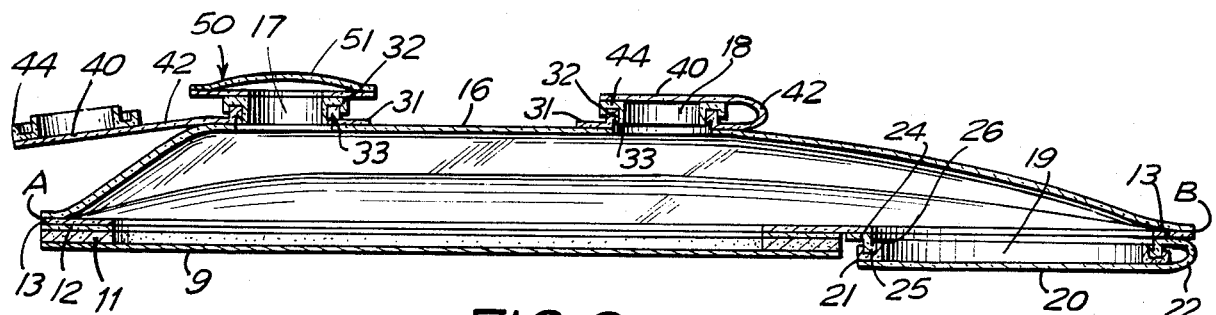
FIG. 2 is a sectional view taken along line 2—2 of FIG. 1.

As shown in FIGS. 1 and 2, bottom pouch wall 13 extends beyond adhesive 11. This extended portion of bottom wall 13 includes an aperture 19 whose functions will be described below. Flange 24 of a polymeric material such as polyethylene is heat sealed to bottom wall 13 around aperture 19. Flange 24 includes a coupling rib 25 that extends outwardly and perpendicularly from flange 24 and a hinge element 22 that is also connected to a cap 20. Cap 20 is also formed of a polymeric material such as polyethylene and includes a channel shaped coupling member 21 that is dimensioned to snap over coupling rib 25. Cap 20 also includes a pull tab 27 to aid in disengaging the coupling elements.

Top pouch wall 16 includes one or more apertures. In the embodiment shown in the figures, top pouch wall 16 has apertures 17 and 18. For ease of construction, apertures 17 and 18 are of identical size and are smaller than aperture 19 in the bottom pouch wall. A flange 31 of polymeric material such as polyethylene is heat sealed to top pouch wall 16 around apertures 17 and 18. Flange 31 includes an outwardly and perpendicularly extending coupling rib 32 and a hinge element 42 that is also connected to a cap 40. Cap 40 is also formed of a polymeric material such as polyethylene and includes a channel shaped coupling member 44 that is dimensioned to snap over coupling rib 32. Cap 40 also includes a pull tab 43 to aid in disengaging the coupling elements.

Coupling ribs 25 and 32 preferably include thin, resilient, deflectible seal strips 26 and 33 which deform into a tight fit within channel shaped coupling members 21 and 44. As shown in FIG. 2, the seal strip preferably extends inwardly from the rib shaped coupling members. However, the coupling system will also be effective if the seal strips extend outwardly from the ribs. Also, in order to increase the security of the seal, the surface of coupling ribs opposite the deflectible seal strip can include a peripheral rim that cooperates with a rim in the channel shaped coupling members. This type of coupling system is described in detail by Steer et al. in British Pat. No. 1,571,657.

Apertures 17 and 18 permit treatment of the patient without the need for first removing and then reattaching the wound drainage device. For example, either or both of caps 40 can be detached and a catheter retaining means or wound irrigation means attached in its place.

Figure 3:
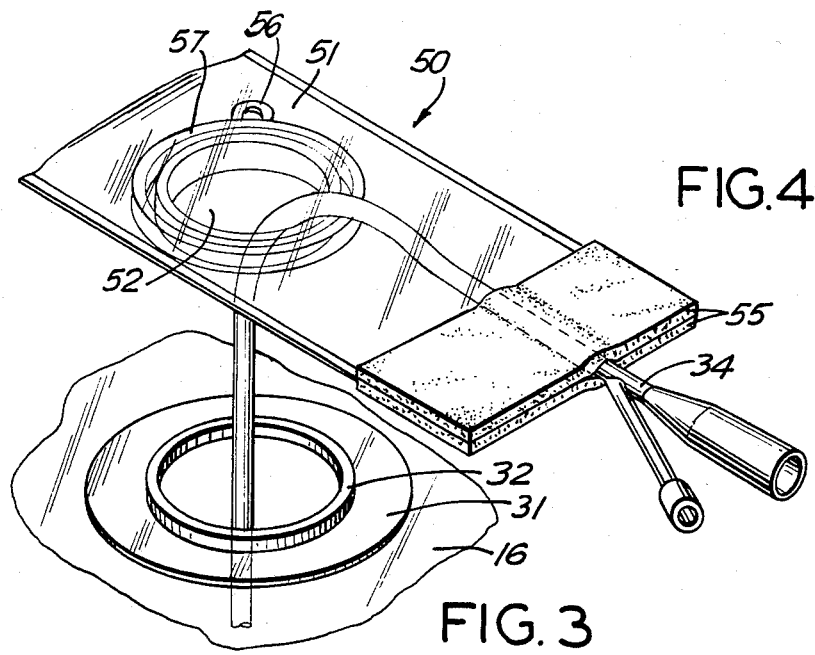
FIG. 3 is a detailed view showing the catheter retainer as it would be attached to the wound drainage pouch.

Catheter retaining means 50 for use with the wound drainage device of this invention is shown in FIGS. 1 to 3. Means 50 consists of a flat tube shaped envelope 51 of polymeric film material such as polyethylene sealed along three edges and having an aperture 52 in one wall. A channel shaped coupling member 57 is heat sealed around aperture 52 and includes a pull tab 56. Channel shaped coupling element 57 is dimensioned to be a snap fit over coupling rib 32. Two strips 55 of polymeric foam such as closed cell polyurethane or polyethylene foam are each coated on one surface with an acrylic adhesive and are attached to the outer surfaces of envelope 51 at the unsealed edge. The foam strips 55 extend beyond the edge of envelope 51 and prior to use the exposed adhesive of the foam strips are covered with peelable release paper. In use, the release papers are removed and the foam strips can then be sealed tightly around a catheter 34 as shown in FIG. 3.

Figure 4:
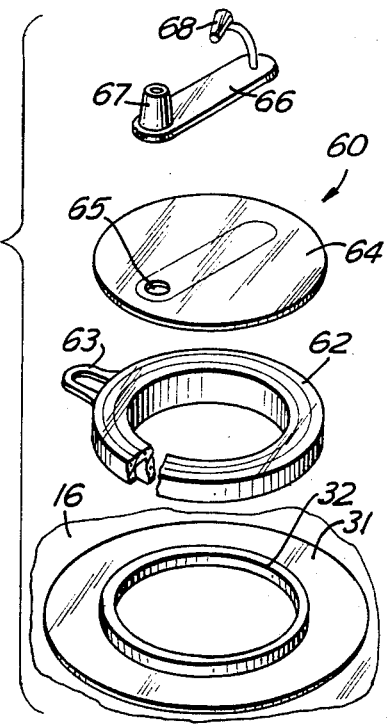
FIG. 4 is an exploded view showing the irrigation port as it would be constructed and attached to the wound drainage pouch.

Wound irrigation means 60 for use with the wound drainage device of this invention is shown in FIG. 4. Means 60 consists of a channel shaped coupling member 62 including a pull tab 63. A disc 64 having an aperture 65 is heat sealed across the back of channel shaped coupling member 62. Element 66 having an upstanding port 67 and a plug type closure element 68 is heat sealed to disc 64 so that port 67 aligns with aperture 65. Channel shaped member 62, disc member 64, and element 66 are formed from a compatible, heat sealable, polymeric material such as polyethylene. Channel shaped coupling member 62 is dimensioned to snap over rib 32. In use, a flexible tube from a source of irrigating fluid (not shown) would be squeezed over port 67. After the irrigation has been completed, the tube would be removed and port 67 would be sealed with plug 68.

The wound drainage and treatment device 10 of this invention is used by first cutting an opening through release paper 9, adhesive layer 11, polymeric film 12, and pouch bottom wall 13 somewhat larger that the wound itself. The release paper is then stripped away and the device is pressed firmly against the patient's body. Aperture 19 is large enough to permit insertion of an average sized hand and this aids in both the cutting and attaching steps. If needed, strips of medical grade adhesive tape can be employed to anchor the edges of the adhesive layer 11.

By keeping cap 20 and caps 40 in place a closed environment is maintained around the wound. When needed, either or both of caps 40 can be removed and replaced by the catheter retainer means or the wound irrigation means.

Aperture 19 serves several functions. In addition to being employed when the wound opening is cut into the device, it provides ready access to the wound without the need for removing the device. Thus, the physician or nurse can reach through this aperture and perform any needed manipulation of the wound area.

Aperture 19 also serves as the exit port for material being drained from the wound. By locating aperture 19 in the bottom pouch wall, gravity can be employed to aid in the drainage operation regardless of whether the device is oriented on the body in a horizontal, vertical, or diagonal position.

Pouch 10 can be drained on an intermittent basis by holding a receptacle beneath aperture 19 and removing cap 20. By squeezing on pouch walls 14 and 15, even heavy fluids can be removed from the pouch. The pouch can also be drained on a continuous basis by removing cap 20 and employing a sleeve (not shown) having at one end a channel shaped coupling member sized to fit over rib 25 and which empties into a storage receptacle at the side of the bed.

The wound drainage device 10 of this invention can be made in various sizes for use with different types of wounds and surgical incisions. A typical size drainage device will have an adhesive layer 11 of about 30 cm. by 14 cm. and the bottom wall 13 will extend about another 15 cm. Aperture 19 will be about 10 cm. in diameter and apertures 17 and 18 will be about 4 cm in diameter.

What is claimed is:

1. A wound care and drainage system comprising a pouch having a bottom wall, top wall, and gusseted side walls, said pouch walls formed from a transparent, moisture proof, odor proof, polymeric film material, a portion of said pouch bottom wall secured to an adhesive layer with the remainder of said pouch bottom wall extending beyond said adhesive layer, said adhesive layer having a thin film of water insoluble polymeric film secured to one surface and said bottom pouch wall secured to said thin polymeric film, bottom wall aperture means in said extended pouch bottom wall that functions as an exit port for material being drained from the wound, the diameter of said bottom wall aperture means of sufficient size so that a hand can be inserted through said bottom wall aperture means into said pouch to aid in locating said pouch on the body and to permit access to the wound area without removing said pouch from the body, and securing means encircling said bottom wall aperture means whereby a cap can be detachably secured to seal said bottom wall aperture means.

2. A wound care and drainage system as in claim 1 wherein said bottom wall aperture means is about 10 cm. in diameter.

3. A wound care and drainage system as in claim 1 wherein said pouch top wall includes one or more top wall aperture means and securing means encircling each of said top wall aperture means whereby a cap can be detachably secured to seal each of said top wall aperture means.

4. A wound care and drainage system as in claim 3 wherein said pouch top wall has two top wall aperture means of approximately the same size.

5. A wound care and drainage system as in claim 4 wherein the diameter of said bottom wall aperture means is at least about twice the diameter of each of said top wall aperture means.

6. A wound care and drainage system as in claim 1 wherein said pouch walls and said thin polymeric film are polyethylene.

7. A wound care and drainage system as in claim 6 wherein said adhesive layer is a homogeneous blend of one or more water soluble or water swellable hydrocolloids dispersed in a viscous elastomeric binder.

8. A wound care and drainage system comprising a pouch having a bottom wall, top wall, gusseted side walls, said pouch walls formed from a transparent, moisture proof, odor proof, polymeric film material, a portion of said pouch bottom wall secured to an adhesive layer with the remainder of said pouch bottom wall extending beyond said adhesive layer, bottom wall aperture means in said extended pouch bottom wall that functions as an exit port for material being drained from the wound, the diameter of said bottom wall aperture means of sufficient size so that a hand can be inserted through said bottom wall aperture means into said pouch to aid in locating said pouch on the body and to permit access to the wound area without removing said pouch from the body, one or more top wall aperture means located in said pouch top wall, a flange of polymeric material sealed to said bottom pouch wall encircling said bottom wall aperture means and one or more flanges of polymeric material sealed to said top pouch wall encircling each of said top wall aperture means, said flanges having an outwardly and perpendicularly extending coupling rib shaped member, and a cap of polymeric material attached by a hinge to each of said flanges, said caps having a channel shaped coupling member dimensioned to snap over the coupling rib shaped member of the corresponding flange.

9. A wound care and drainage system as in claim 8 wherein said coupling rib shaped members have a thin, resilient, deflectible seal strip which deforms into a tight fit within said channel shaped coupling members.

10. A wound care and drainage system as in claim 9 wherein said seal strips extend inwardly from said coupling rib shaped members.

11. A wound care and drainage system as in claim 9 wherein said seal strips extend outwardly from said coupling rib shaped members.

12. A wound care and drainage system as in claim 8 wherein a catheter retaining means is detachably secured to one of said pouch top wall apertures.

13. A wound care and drainage system as in claim 12 wherein said catheter retaining means comprises a flat envelope of polymeric material sealed along three edges and having an aperture in one wall of said envelope, a channel shaped coupling member secured to said envelope around said aperture, said channel shaped coupling member dimensioned to snap over the coupling rib shaped member projecting from the flange secured around said pouch top wall aperture, and strips of polymeric foam material secured to the surfaces of said envelope near the open end of said envelope, said strips of foam coated with an adhesive material so that the foam strips can be pressed into tight contact with a catheter.

14. A wound care and drainage system as in claim 8 wherein a wound irrigation means is detachably secured to one of said pouch top wall apertures.

15. A wound care and drainage system as in claim 14 wherein said wound irrigation means comprises a channel shaped coupling means dimensioned to snap over the coupling rib shaped member projecting from the flange secured around said pouch top wall aperture, a disc having an aperture secured across the back of said channel shaped coupling means, and an element having an upstanding port and a plug secured to said disc so that said port and said disc aperture are aligned.

16. A wound car and drainage system as in claim 8 wherein said pouch has two top wall aperture means of approximately the same size and the diameter of said bottom wall aperture means is at least about twice the diameter of each of said top wall apertures.

17. A wound care and drainage system as in claim 16 wherein said bottom wall aperture means is about 10 cm in diameter.

18. A wound care and drainage system as in claim 8 wherein said adhesive layer has a thin film of water insoluble polymeric material secured to one surface and said bottom pouch wall is secured to said thin polymeric film.

* * * * *